United States Patent
Rzany et al.

(10) Patent No.: US 10,537,662 B2
(45) Date of Patent: *Jan. 21, 2020

(54) METHOD FOR PREPARING BIOLOGICAL TISSUE

(71) Applicant: BIOTRONIK AG, Buelach (CH)

(72) Inventors: Alexander Rzany, Nuremberg (DE); Wilhelm Erdbruegger, Constance (DE)

(73) Assignee: Biotronik AG, Buelach (DE)

( * ) Notice: Subject to any disclaimer, the term of this patent is extended or adjusted under 35 U.S.C. 154(b) by 403 days.

This patent is subject to a terminal disclaimer.

(21) Appl. No.: 15/193,658

(22) Filed: Jun. 27, 2016

(65) Prior Publication Data

US 2016/0303289 A1 Oct. 20, 2016

Related U.S. Application Data

(63) Continuation-in-part of application No. 14/341,783, filed on Jul. 26, 2014, now Pat. No. 9,402,934, and a continuation-in-part of application No. 15/170,528, filed on Jun. 1, 2016.

(30) Foreign Application Priority Data

Jul. 31, 2013 (EP) .................................... 13178696
Jun. 8, 2015 (DE) ........................ 10 2015 108 952

(51) Int. Cl.
*A61F 2/24* (2006.01)
*A61L 27/36* (2006.01)

(52) U.S. Cl.
CPC ........ *A61L 27/3687* (2013.01); *A61F 2/2415* (2013.01); *A61L 27/367* (2013.01); *A61L 27/3625* (2013.01); *C12Y 302/01022* (2013.01); *A61L 2430/20* (2013.01); *A61L 2430/40* (2013.01)

(58) Field of Classification Search
CPC ............. A61L 27/3687; A61L 27/3625; A61L 27/367; A61L 2430/20; A61L 2430/40; A61L 27/3633; A61L 27/3604; A61L 27/24; A61L 27/3683; A61L 17/08; A61L 17/005; A61L 2300/414; A61L 31/16; A61F 2/2415; A61F 2002/30766; C12Y 302/01022; A61K 35/12; A61K 35/44; A61K 35/34; A61K 35/28; C12N 2533/54; C12N 5/0654; C12N 5/0697
See application file for complete search history.

(56) References Cited

U.S. PATENT DOCUMENTS

| | | | |
|---|---|---|---|
| 5,336,616 A | 8/1994 | Livesey et al. | |
| 9,402,934 B2 * | 8/2016 | Rzany | A61L 27/24 |
| 2010/0030340 A1 | 2/2010 | Wolfinbarger et al. | |
| 2012/0189588 A1 | 7/2012 | Nahas et al. | |
| 2012/0328592 A1 | 12/2012 | Shulman et al. | |
| 2013/0158676 A1 | 6/2013 | Hayzlett et al. | |
| 2013/0190893 A1 | 7/2013 | Roock et al. | |
| 2015/0252930 A1 | 9/2015 | Martin | |

FOREIGN PATENT DOCUMENTS

| | | | | |
|---|---|---|---|---|
| EP | 2832379 A1 * | 2/2015 | | A61L 27/24 |
| EP | 2832379 A1 | 2/2015 | | |
| KR | 20120002379 A | 1/2012 | | |
| WO | 2002/49681 A1 | 6/2002 | | |
| WO | 2004/052417 A1 | 6/2004 | | |
| WO | 2005/118014 | 12/2005 | | |
| WO | 2011/109433 | 9/2011 | | |

OTHER PUBLICATIONS

PArk s, et al "Removal of Alpha-Gal Epitopes from Porcine Aortic Valve and Pericardium using Recombinant Human Alpha Galactosidase A" J Korean Med Sci. Dec. 2009; 24(6): 1126-1131; PMID: 19949670. (Year: 2009).*
Int J Cardiol. "Novel self-expandable, stent-based transcatheter pulmonic valve: a preclinical animal study." Apr. 15, 2014 (Epub Feb. 20, 2014);173(1):74-9; doi: 10.1016/j.ijcard.2014.02.005. (Year: 2014).*
Everaerts, F.J.L. "A Novel Approach in Cross-linking of Bioprosthetic Heart Valves." Thesis, University of Twente, 2007, 150 pp.
Pratt, W.B. "Antibiotics that Affect Membrane Permeability: Polymyxin B, Colistin, and Gramicidin A." The Antimicrobial Drugs, 2000, Chapter 8, pp. 234-241.
Youngstrom et al. "Functional Characterization of Detergent-Decellularized Equine Tendon Extracellular Matrix for Tissue Engineering Applications." PLoS ONE, May 27, 2013, 8(5): e64151, pp. 1-9.

* cited by examiner

*Primary Examiner* — Aaron J Kosar
(74) *Attorney, Agent, or Firm* — Wagenknecht IP Law Group PC

(57) ABSTRACT

A method for preparing tissue for medical applications, including decellularizing the tissue by means of a detergent, characterized in that the decellularizing detergent contains at least one amphiphilic lipopeptide; treating the decellularized tissue with an α-galactosidase; and cross-linking the collagen fibers of the treated tissue by means of a suitable cross-linking agent.

14 Claims, 8 Drawing Sheets

*STAND DER TECHNIK*

STAND DER TECHNIK

METHOD FOR PREPARING BIOLOGICAL TISSUE

CROSS-REFERENCE TO RELATED APPLICATIONS

This application is a continuation-in-part of U.S. patent application Ser. No. 14/341,783 filed Jul. 26, 2014, which claims benefit of priority to European patent application EP 13178696.4, filed Jul. 31, 2013: the contents of both are herein incorporated by reference in their entirety.

This application is also a continuation-in-part of U.S. patent application Ser. No. 15/170,528, filed Jun. 1, 2016, which claims benefit of priority to German patent application DE 10 2015 108 952.1 filed Jun. 8, 2015; the contents of both are herein incorporated by reference in their entirety

FIELD OF THE INVENTION

The present invention relates to a method for preparing tissue for medical applications, in particular for preparing tissue for use in an artificial heart valve, including the steps of decellularizing the tissue by means of a suitable detergent, treating the decellularized tissue with an α-galactosidase, and subsequently cross-linking the collagen fibers of the treated tissue by means of a suitable cross-linking agent.

BACKGROUND OF THE INVENTION

There are basically two different types of heart valve prostheses: Prostheses comprising mechanical valves, which are artificially produced, usually being made of graphite coated with pyrolytic carbon, and prostheses comprising valves made of biological tissue, usually pericardial tissue, which is usually obtained from animal sources (e.g. swine or cattle). The heart valve formed of biological tissue is usually mounted in a base body (e.g. a rigid plastic framework or a self-expanding stent), which is then implanted at the position of the natural valve. The present invention describes a method for preparing such tissue for use in a heart valve prosthesis for implantation at the site of a natural heart valve.

The tissue of origin must be thoroughly cleaned and prepared before implantation. In so doing, the tissue is modified, to the greatest extent possible, such that the tissue is not recognized by the body as foreign tissue, is not calcified, and has the longest life span possible. Such a method for preparing tissue substantially comprises at least two main steps having a plurality of intermediate rinsing processes.

The first essential preparation step is the so-called decellularization of the tissue. In this step, cell membranes, intracellular proteins, cell nuclei, and other cellular components are removed as completely as possible from the tissue in order to obtain the purest extracellular matrix possible. Any cells and cellular components remaining in the tissue would be potent crystal nuclei, in particular, for an unwanted calcification of the biological implant material. The decellularization, as a washing step, should be performed in a manner that is so gentle that the structure and the collagen fibers in the extracellular matrix remain as unaffected as possible while ensuring that all cells contained therein are thoroughly removed from the tissue.

The second essential preparation step is that of cross-linking the tissue, in particular the collagen fibers. After decellularization, preferably all cellular components have been removed from the tissue and the biological material nearly exclusively comprises the extracellular matrix. In the case of pericardial tissue, the extracellular matrix is formed primarily of collagen fibers. In order to obtain biological material having the most optimal mechanical properties possible and to prevent rejection reactions by the receiving body, the collagen fibers are cross-linked by means of a suitable cross-linking agent via the incorporation of chemical bonds. The cross-linking agent binds to the amino groups of the collagen fibers and forms chemically stable compounds between collagen fibers. A biological material having long-term stability is thereby obtained from the three-dimensionally arranged collagen fibers, wherein this biological material is no longer recognized as foreign biological material. The stability and strainability of the tissue is markedly increased by means of the three-dimensional cross-linking or linking of the individual collagen fibers via the cross-linking agent. This is decisive, in particular, in the case of use as tissue of a heart valve, where the tissue must open and close, in brief intervals, as a valve.

An alternative method for preparing biological tissue is described in WO 2004/052417. In this method according to the prior art, the tissue is decellularized with a 1-2% deoxycholic acid solution. After a plurality of rinsing steps, the tissue is conditioned in a solution containing a cyclic lipopeptide. The cyclic lipopeptide surfactin is used, in particular, as the conditioning agent after decellularization is completed and before repopulation with cells. In this alternative method according to the prior art, cross-linking of the collagen fibers is not performed using a suitable cross-linking agent. After conditioning, the tissue is populated with natural cells.

WO 2011/109433 discloses a method for preparing biological tissue, wherein distilled water is used for decellularization. Glutaraldehyde functions as the cross-linking agent in a subsequent step.

WO 2005/118014 discloses the use of a first ionic detergent and a second non-ionic detergent for decellularization. In this case, an anionic detergent such as sodium dodecyl sulfate or sodium dodecyl sulfonate is preferably provided as the first ionic detergent. As an alternative, bile acids such as sodium cholate or sodium deoxycholate can be used as the first detergent. The second detergent is electrically neutrally charged, such as a detergent containing polyethylene glycol.

While strong detergents may thoroughly decellularize tissue, they also tend to weaken the mechanical properties of the tissue itself. However, using more gentle detergents risks incomplete decellularization or incomplete removal of cellular components, thereby leaving antigenic moieties on the tissue. We have found that the above-mentioned calcifications can still occur even in spite of carefully performed decellularization procedures and can originate, inter alia, in antibodies directed against galactose-α-1,3-galactose-β-1,4-N-acetylglucosamine epitopes (α-gal epitopes on the surface of the implanted tissue). Here, α-gal epitopes can lead to severe immune responses that encourage calcification. The concentration of α-gal epitopes on the surface could be reduced in principle by harsh decellularization conditions, but this would have a significantly negative influence on the mechanical properties of the valve material. In order to minimize calcifications and provide tissue having significantly improved mechanical properties, it would therefore be desirable to provide tissue that has been subjected to gentle decellularization and with which α-gal epitopes on the surface of the tissue have been fully removed where possible.

Accordingly, there remains a need for improved methods for the treatment of biological tissue to prevent or reduce calcification while improving or maintaining the mechanical stability of tissue for implantation.

SUMMARY OF THE INVENTION

The invention provides improved methods of preventing or reducing calcification of tissue while maintaining significant mechanical integrity. In particular, the invention provides a method for preparing biological tissue such that cellular components are removed from the tissue in a thorough yet gentle manner such that subsequent cross-linking produces a mechanically stable and long-lived tissue, which is suitable, in particular, for use as tissue of an artificial heart valve.

The stated problem is solved, in terms of a method for preparing tissue for medical applications, in particular tissue for use for an artificial heart valve, including: decellularizing the tissue by means of a detergent, treating the tissue with an α-galactosidase, and cross-linking the collagen fibers of the treated tissue by means of a suitable cross-linking agent; characterized in that the detergent for decellularization contains at least one lipopeptide having amphiphilic properties, preferably comprising a hydrophilic base structure and a hydrophobic side chain. The stated problem is solved, in terms of the application, at least in part by use of a solution containing at least one lipopeptide having amphiphilic properties, preferably comprising a hydrophilic basic structure and a hydrophobic side chain, as the detergent for the decellularization of biological tissue, in particular biological tissue for heart valve prostheses, followed by treatment of the tissue with an α-galactosidase. Advantageous embodiments of the inventions are described herein.

The invention is described in the following using the example of a method for preparing tissue for use for an artificial heart valve. Although the present invention is particularly suitable for preparing this type of tissue, it is not limited to this application. The present invention can also be used to prepare blood vessels, bone, cartilage, ligaments, or other tissue at risk of calcification.

The invention further relates to a use for at least one solution containing lipopeptides and at least one solution containing an α-galactosidase.

The fundamental concept of the invention is the use of lipopeptides as detergent for decellularization followed by treatment with an α-galactosidase. According to the inventive concept, peptides, lipopeptides containing β-hydroxy fatty acids or β-amino fatty acids are not used for conditioning, but rather as detergent for decellularization. Surprisingly, it has been shown that a combined treatment with lipopeptides and an α-galactosidase yield excellent results in the decellularization of tissue. The tissue is freed of cellular components in a markedly more gentle manner. When a detergent and an α-galactosidase according to the invention is used, the structure of the extracellular matrix is retained to a markedly better extent than is the case with a detergent according to the prior art. The detergent according to the invention therefore contains at least one lipopeptide having amphiphilic properties, preferably comprising a hydrophilic base structure and a hydrophobic side chain to gently decellularize the tissue. Afterwards the α-galactosidase removes remaining α-gal epitopes. As a result, the subsequent cross-linking step results in a tissue having mechanical properties that are markedly improved over the prior art and which is therefore suited for use, in particular, for use in a heart valve prosthesis.

Particularly preferably, the detergent for decellularization contains a cyclic lipoheptapeptide, in particular surfactin. In this preferred embodiment of the invention, a detergent containing surfactin is used for decellularization. In particular, the detergent contains surfactin having a cyclic structure, as indicated in the following:

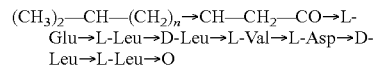

Therein, n=8-12, preferably 9, and Glu, Leu, Val, Asp stand for the amino acids glutamic acid, leucine, valine, and aspartic acid.

Other advantageous lipopeptides include daptomycin, caspofungin, arthrofactin, echinocandins, iturins, syringomycins, syringopeptides, and/or polymyxins. Advantageously, the detergent contains at least one lipopeptide selected from the list: surfactin, daptomycin, caspofungin, arthrofactin, or the group of echinocandins, iturins, syringomycins, syringopeptides, polymyxins.

Advantageously, the tissue is rinsed before and, particularly preferably, after decellularization at least once, preferably a plurality of times, with a suitable solvent, in particular a buffered saline solution and/or an alcohol solution. Buffered sodium chloride solutions and/or an ethanol solution are particularly advantageous. In some embodiments at least one rinse, in particular a buffered saline solution, after decellularization includes α-galactosidase.

Particularly preferably, the detergent comprises a buffer solution, particularly preferably a phosphate buffer solution, advantageously at pH 7.4, which contains the lipopeptide, in particular surfactin, at a concentration of 100 mg/l to 2000 mg/l, preferably 500 mg/l to 700 mg/l, particularly preferably 600 mg/l. The use of Dulbecco's phosphate buffered saline (DPBS) without calcium and magnesium as the carrier solution for the detergent surfactin is particularly advantageous. Other biological buffer solutions, such as Tris(hydroxymethyl)aminomethane (TRIS)- or 2-(4-(2-hydroxyethyl)-1-piperazinyl)-ethanesulfonic acid (HEPES)-buffered solutions are also advantageous.

The present invention further relates to the use of a solution containing at least one lipopeptide having amphiphilic properties, preferably comprising a hydrophilic basic structure and a hydrophobic side chain, as the detergent for the decellularization of biological tissue, in particular biological tissue for heart valve prostheses. According to the invention, a solution containing at least one lipopeptide is not used for conditioning, but rather is used for the decellularization and purification of biological tissue.

Surprisingly, it has been shown that solutions containing lipopeptides decellularize biological tissue in a thorough yet gentle manner. It was also surprising to find that still further improved decellurization was achieved after treatment with an α-galactosidase.

The use of a solution containing, at least, surfactin, daptomycin, caspofungin, arthrofactin, an echinocandin, an iturin, a syringomycin, a syringopeptide, and/or a polymyxin as the detergent for the decellularization of biological tissue is particularly advantageous.

It is advantageous for surfactin, daptomycin, caspofungin, arthrofactin and/or an echinocandin, iturin, syringomycin, syringopeptide, polymyxin to be dissolved in a buffer solution, in particular a phosphate buffer solution. TRIS- or HEPES-buffered solutions are also advantageous.

After primary decellularization with detergent, further treatment with at least one α-galactosidase removes remaining α-gal epitopes from the surface of the tissue, and the risk of subsequent calcification can be significantly reduced or even minimized. In a preferred embodiment the tissue is treated with one α-galactosidase. However, it is likewise possible to use a combination of α-galactosidases. This means that the α-galactosidases used in combination have a different structure and/or origin; i.e. the α-galactosidases have been produced in a different living organism and/or have a different structure.

The invention provides that α-galactosidases, also α-D-galactoside galactohydrolases, E.C. 3.2.1.22, are enzymes that are able to catalyze the hydrolysis of galactosyl residues of the non-reducing ends of a multiplicity of oligosaccharides and polysaccharides and also of galactolipids and glycoproteins. With regard to tissue, α-galactosidases can be used to remove α-1,3-galactosyl residues on and in the tissue. It has been found here that α-gal epitopes can be effectively removed from the surface of the tissue by treatment with α-galactosidases, whereby immune responses and calcifications can be reduced.

It is also provided that α-galactosidases can vary significantly in terms of their purpose, structure and effect, depending on their origin. This is strongly associated with the fact that a multiplicity of organisms produce α-galactosidases, such as archaea, bacteria, fungi, plants or animals. A possible grouping of α-galactosidases may lie in the purpose of the organism in question. Here, a grouping may be given for example by the pH-dependency of the enzyme activity. The inventors have found that not all α-galactosidases are equally suitable for the treatment of tissue for use in heart valves. Rather, the inventors have surprisingly found that certain α-galactosidases are suitable in particular for use in the method proposed herein.

In a preferred embodiment the use of alkaline α-galactosidases is provided for the methods herein. Alkaline α-galactosidases are characterized in that they have a high or their highest enzymatic activity in alkaline medium and also have a high substrate specificity. The use of alkaline α-galactosidases is advantageous, since it is thus made possible to also use DNases and RNases parallel to the alkaline α-galactosidases. DNases and RNases are used for the removal of residual ribonucleic acids from the tissue, which may also contribute to a calcium binding. By combination of α-galactosidases with DNases and/or RNases, an even more improved protection against calcification can thus be achieved, in particular in a pH range from 7.1 to 8.0, more preferably in a pH range from 7.2 to 7.8, and most preferably that demonstrate the highest specific enzyme activity in a pH range from 7.3 to 7.6. Preferred alkaline α-galactosidases originate from *Arabidopsis thaliana, Cucumis melo, Cucumis sativus, Oryza sativa*, for example the *Japonica* group, *Pisum sativum, Solanum Lycopersicum, Tetragonia tetragonioides* and *Zea mays*.

In a further preferred embodiment α-galactosidases from the GH-36 family are used in the methods. It has been found that representatives of the GH-36 family can remove α-gal epitopes on tissue highly efficiently. The inventors have surprisingly found that α-galactosidases from the GH-36 family can remove α-gal epitopes on tissue more quickly and at lower concentrations than representatives from other GH families.

In a further preferred embodiment α-galactosidases from the GH-36 family, sub-group II, are used in the methods. Representatives of this sub-group have proven to be particularly suitable for efficiently removing α-gal epitopes on tissue. Preferred α-galactosidases from the GH-36 family, sub-group II, are based on the following sources, selected from the group comprising or consisting of *Oryza sativa* of the *Japonica* group, *Cucumis melo, Bifidobacterium breve* C50, *Sulfolobus solfactarius* and *Sulfolobus tokodaii*. In a particularly preferred embodiment of the method proposed herein, the α-galactosidase originates from *Cucumis melo*.

It has been found in particular that α-galactosidases of *Cucumis melo* are able to remove α-gal epitopes on tissue more specifically than, for example, α-galactosidases of green coffee bean (GCB) or the acidic variant of *Aspergillus niger*.

As presented above, the proposed method can have additional steps besides the treatment of tissue with α-galactosidases. This is advantageous in particular in respect of the acquisition of a tissue that has both excellent mechanical properties and low to no tendency towards calcification.

After α-galactosidase treatment, the collagen fibers of the tissue is crosslinked by means of a suitable crosslinking agent. The cross-linking agent preferably contains glutaraldehyde. In alternative embodiments of the invention, the cross-linking agent contains carbodiimide, formaldehyde, glutaraldehyde acetals, acyl azides, cyanimide, genipin, tannin, pentagalloyl glucose, phytate, proanthocyanidin, reuterin and/or epoxide compounds The present invention provides, in particular, a method for preparing biological tissue, which ensures thorough and reliable decellularization, which is simultaneously implemented in a manner that is gentle on tissue such that the mechanical properties of the tissue, after decellularization, α-galactosidases treatment, and cross-linking, are markedly improved over the prior art.

The method according to the invention for the preparation of biological tissue, in particular for the preparation of biological tissue for use in a heart valve prosthesis, minimizes the risk of calcification of the tissue (and, therefore, the prosthesis) in clinical use. The properties of the tissue are positively influenced in a decisive manner by the detergent for decellularization that is used according to the invention. A tissue that has been prepared using the method according to the invention exhibits markedly improved mechanical strainability.

BRIEF DESCRIPTION OF THE DRAWINGS

Those skilled in the art will recognize that the drawings described below are for illustrative purposes only. The drawings are not intended to limit the scope of the invention but to provide exemplary embodiments

DETAILED DESCRIPTION OF PREFERRED EMBODIMENTS

The invention is explained in greater detail in the following by reference to exemplary embodiments in the figures and is compared with a method according to the prior art.

In one exemplary embodiment of the invention, a biological tissue is obtained from porcine pericardial tissue by mechanical removal of adhering foreign tissue and subsequent rinsing in isotonic saline solution (Fresenius-Kabi) for 20 hours. This tissue is subjected to decellularization with a detergent comprising a DPBS solution without calcium/magnesium (Lonza; DPBS w/o Ca++/Mg++; Art. No. 17-512) and surfactin (Sigma-Aldrich, surfactin from *Bacillus subtilis*, Art. No. 53523) in a concentration of 600 mg/l.

The aforementioned exemplary embodiment according to the present invention is compared with two detergents according to the prior art.

In the first example according to the prior art, the biological tissue is subjected to decellularization with a detergent containing sodium dodecyl sulfate (SDS; Sigma-Aldrich, Art. No. L3771) in a concentration of 5 g/l. The solvent used in this case as well is DPBS solution without calcium/magnesium (Lonza; DPBS w/o Ca++/Mg++; Art. No. 17-512).

In a second example according to the prior art, the biological tissue is subjected to decellularization with a detergent containing deoxycholic acid (DCA; Sigma-Aldrich, Art. No. D6750) in a concentration of 10 g/l. Isotonic saline solution (Fresenius-Kabi) is used as the solvent in this case.

Figure 1:
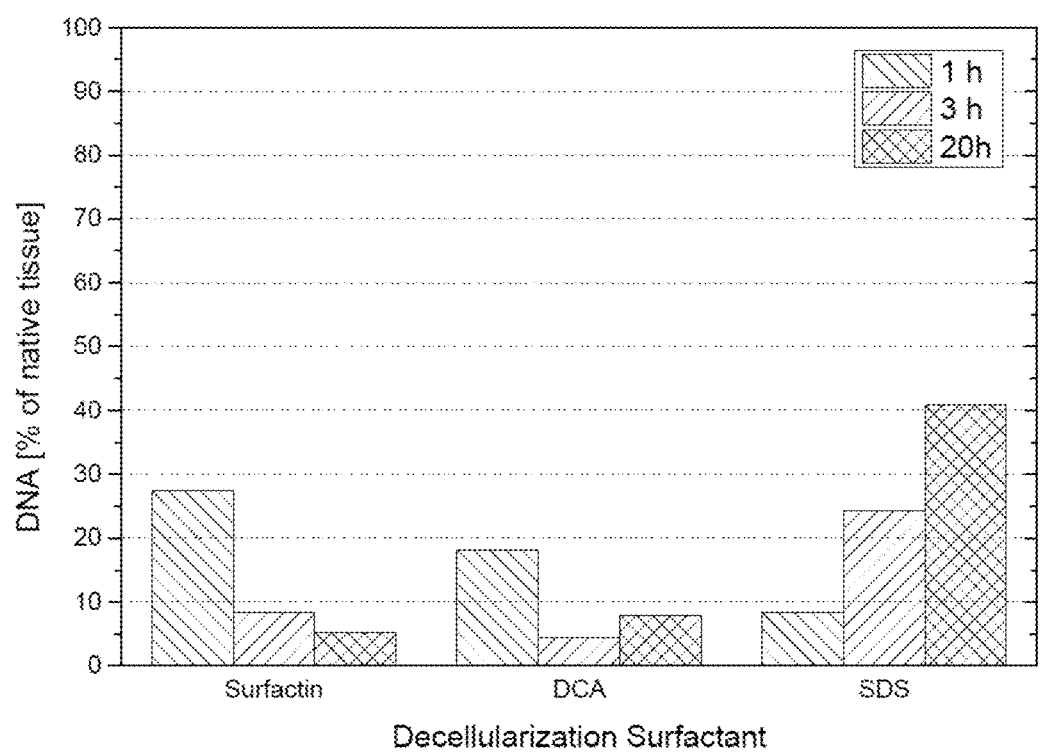
FIG. 1 is a chart depicting a comparison of the DNA content of decellularized tissue treated with surfactin, DCA or SDS.

FIG. 1 shows the comparison of the DNA content after decellularization between the exemplary embodiment according to the invention and the two examples according to the prior art. In FIG. 1, the DNA content of the pericardial tissue after decellularization is plotted on the ordinate in % of the original DNA content before decellularization. In each case, the DNA content was plotted after the biological tissue had been in the respective washing solution for 1 hour, 3 hours, and 20 hours. The DNA content is a direct measure of the removal of cellular components from the biological tissue.

With the aid of the detergent for decellularization containing DCA, the DNA content is reduced to approximately 4% after three hours. As is evident in FIG. 1, the DNA content can be reduced to a similar value after 20 hours in the surfactin-containing detergent of the exemplary embodiment of the invention. The extent of decellularization of pericardial tissue achieved with surfactin within 20 hours corresponds to that of deoxycholic acid. The values of the DNA content for the detergent containing SDS are comparable in this case only to a limited extent, since SDS induces a very pronounced structural change of proteins and massively impairs the DNA detection method, with clearly visible decellularization.

Figure 2:
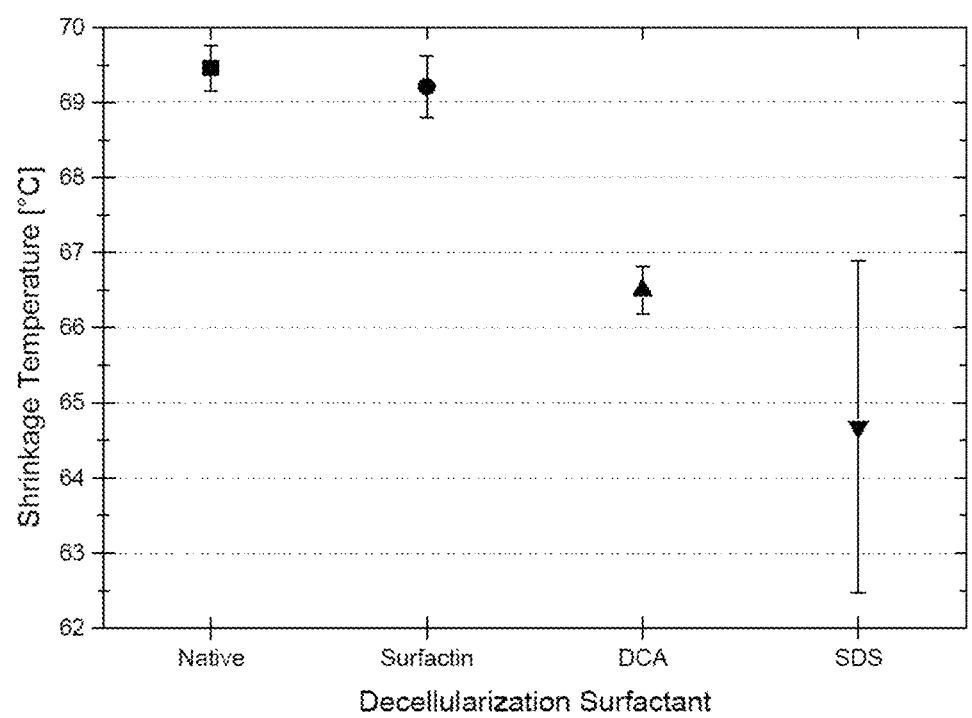
FIG. 2 is a chart depicting the shrinkage temperature of the decellularized tissue after treatment with surfactin, DCA or SDS compared to the shrinkage temperature of native tissue.
Figure 3A:
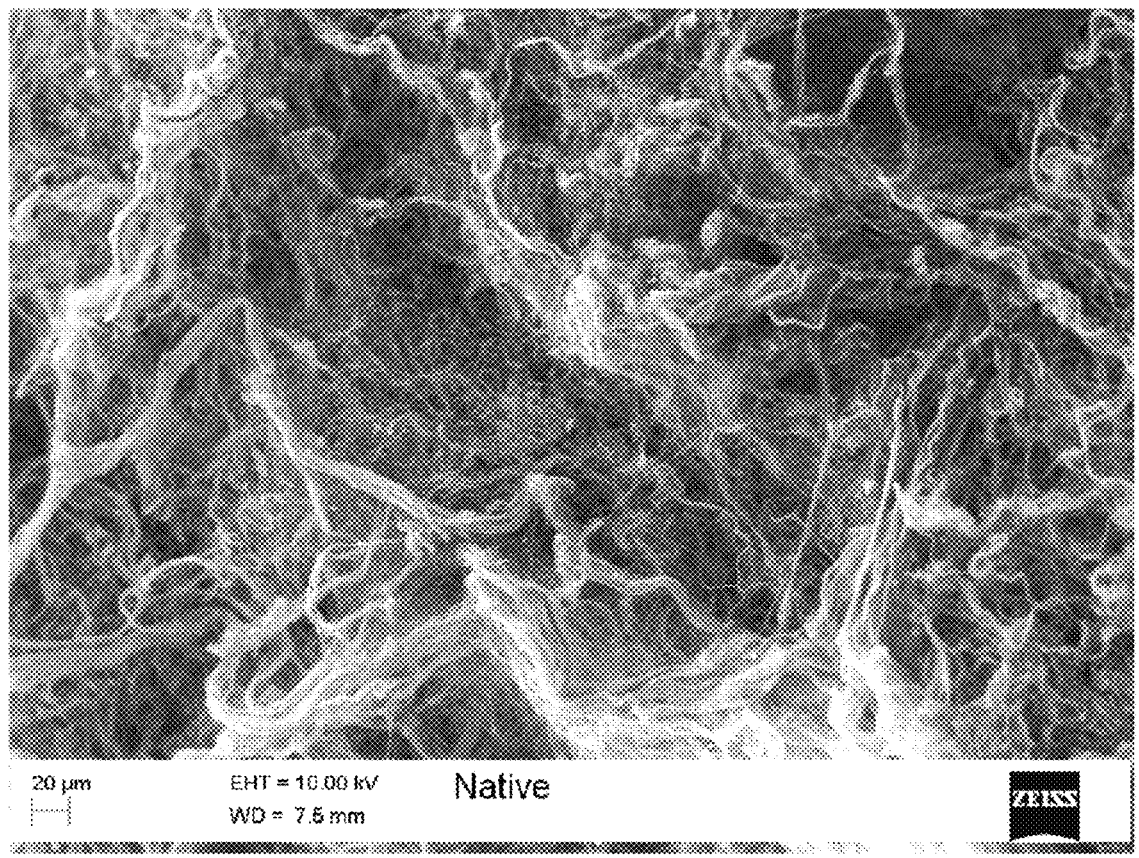
FIGS. 3a-3d are electron-microscopic images of native tissue (FIG. 3a), and decellularized tissue treated with surfactin (FIG. 3b), DCA (FIG. 3c) and SDS (FIG. 3d).
Figure 3B:
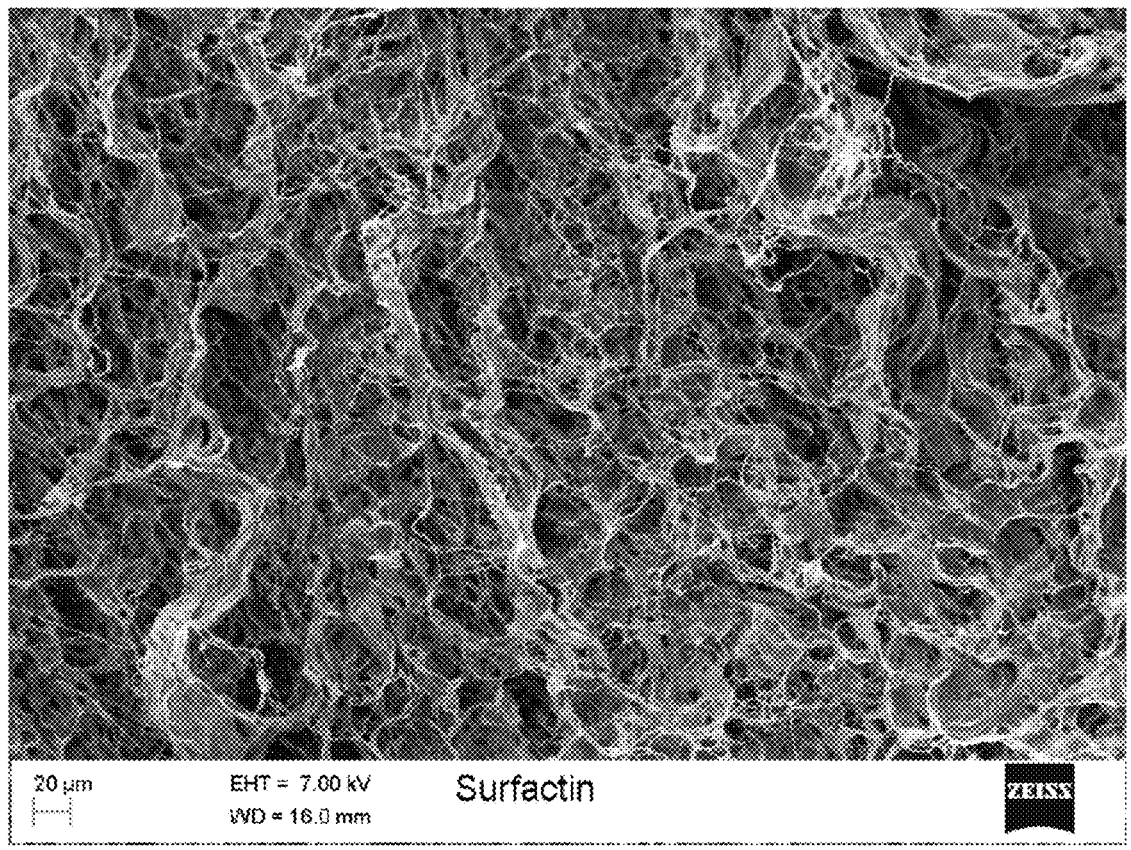
Figure 3C:
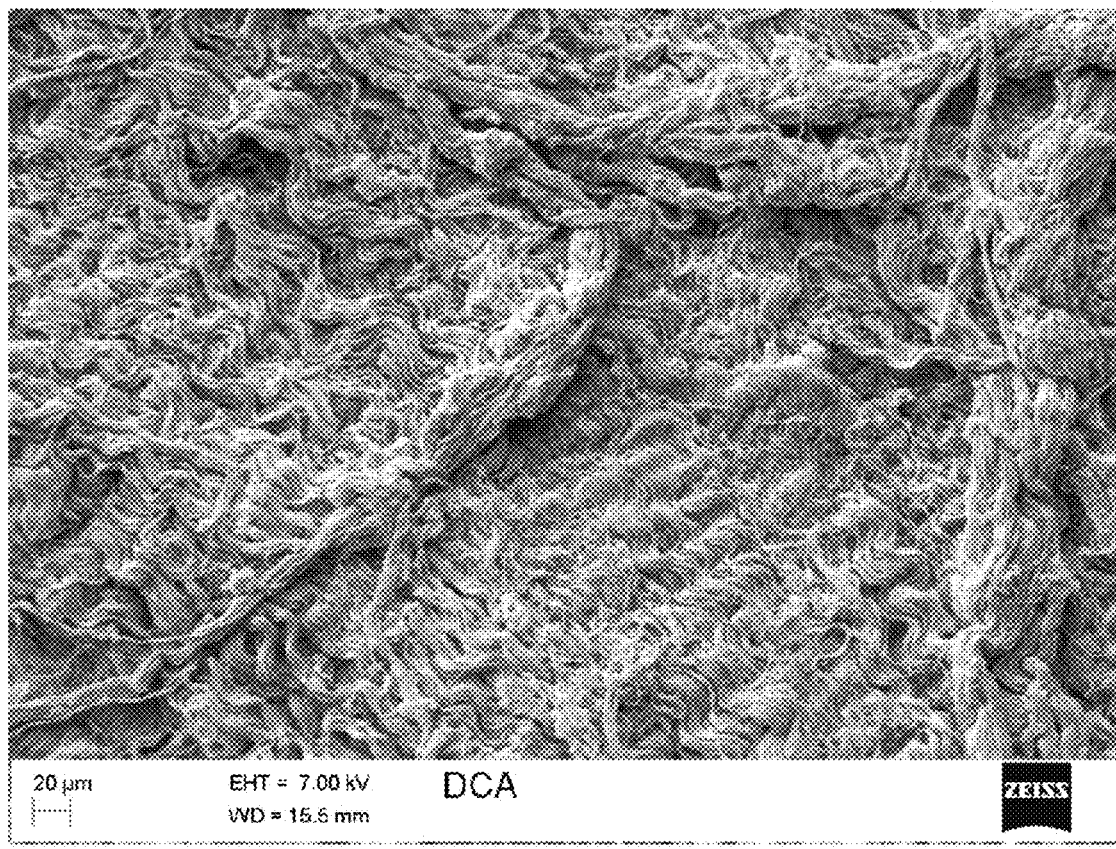
Figure 3D:
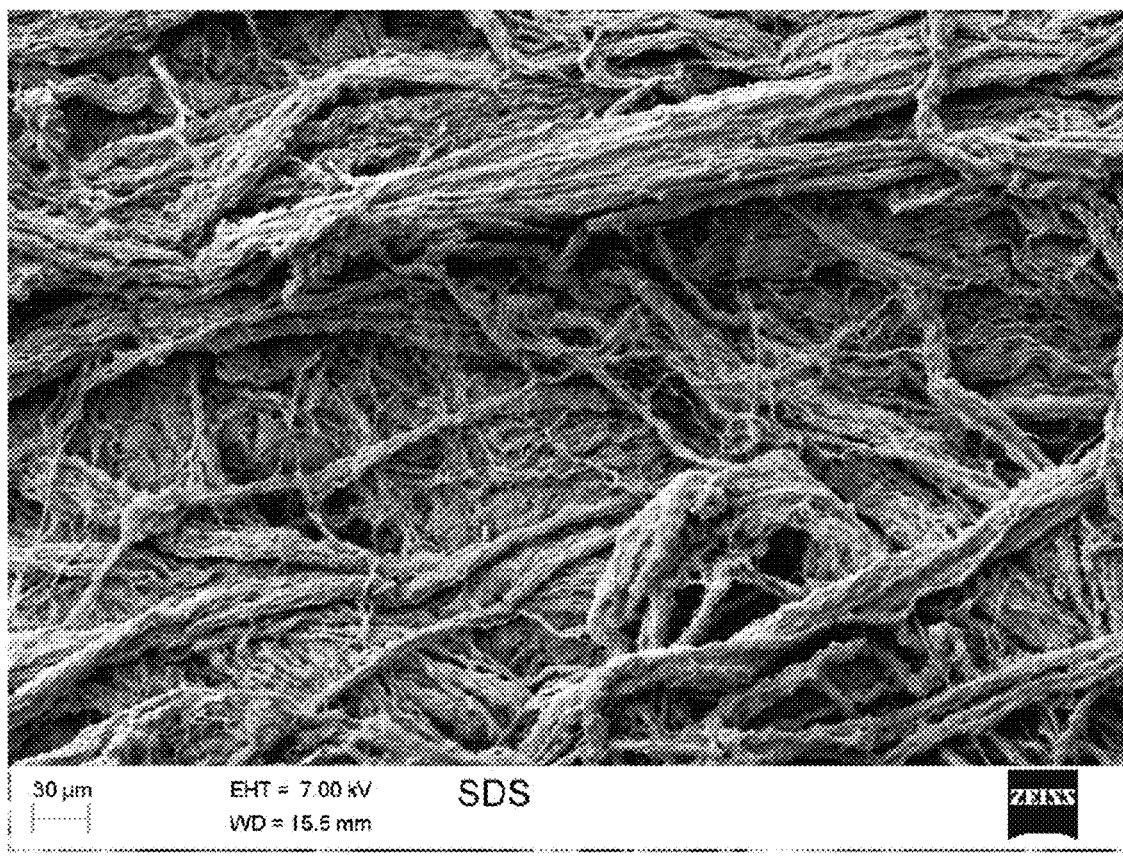

The serious advantages of the method according to the invention compared to decellularization processes according to the prior art are shown in FIG. 2 through FIG. 3d.

FIG. 2 shows, on the ordinate (enlarged scale, zero point not shown), the shrinkage temperature of the decellularized tissue after treatment with the three aforementioned detergents as compared to the shrinkage temperature of the native tissue.

Due to the dominant portion of collagen in the extracellular matrix of pericardial tissue, the shrinkage temperature is the temperature at which the protein thermally denatures collagen, i.e. irreversibly changes the spatial structure thereof. As a result of the structural change of the collagen molecules, the tissue undergoes massive, irreversible structural changes, which become less pronounced, as is clearly visible, when the shrinkage temperature is reached.

The shrinkage temperature was determined in experimentation by means of differential scanning calorimetry (DSC). In this method, the temperature of the sample to be measured is increased linearly over time and the flow of heat into or out of the sample is measured relative to a reference sample. If thermodynamic processes occur in the sample, e.g. the irreversible structural change of the collagen, a distinct peak forms at the shrinkage temperature in the thermogram that is measured. The level of the shrinkage temperature is a direct indicator of the stability of the spatial structure of the collagen molecules. The least possible change compared to the state in native tissue is therefore a direct indication, at the molecular level, of the markedly more gentle decellularization by surfactin.

As is clearly evident in FIG. 2, the shrinkage temperature of the pericardial tissue after decellularization according to the exemplary embodiment of the invention is nearly identical to the shrinkage temperature of the untreated native pericardial tissue. The decellularization according to the two exemplary embodiments of the prior art with DCA and SDS, however, result in a shrinkage temperature that is markedly reduced, by 3° C. and 5° C., respectively, and, therefore, to a markedly impaired tissue structure. The mechanical properties of the native biological tissue and the tissue after decellularization according to the invention are therefore very similar. With the aid of the method according to the invention, the decellularization therefore takes place in a very gentle method, as demonstrated.

The different impairment of the tissue structure is also shown in the electron-microscopic images of the native tissue and the tissue after decellularization with the aforementioned detergents, wherein these images are shown in FIGS. 3a-d.

The images exhibit great similarity in the comparison of the native tissue in FIG. 3a with the decellularized tissue according to the aforementioned exemplary embodiment of the invention in FIG. 3b. Both tissues show a plurality of collagen fibers and strands that are separated from one another.

By comparison, the tissue shown in FIG. 3c and FIG. 3d is markedly changed after decellularization with the stated detergents according to the prior art. Smaller collagen fibers, in particular, tend to attach themselves to one another in this case. As a result, the tissue structure is markedly changed and, in the electron-microscopic images, appears to be much more compact.

Figure 4:
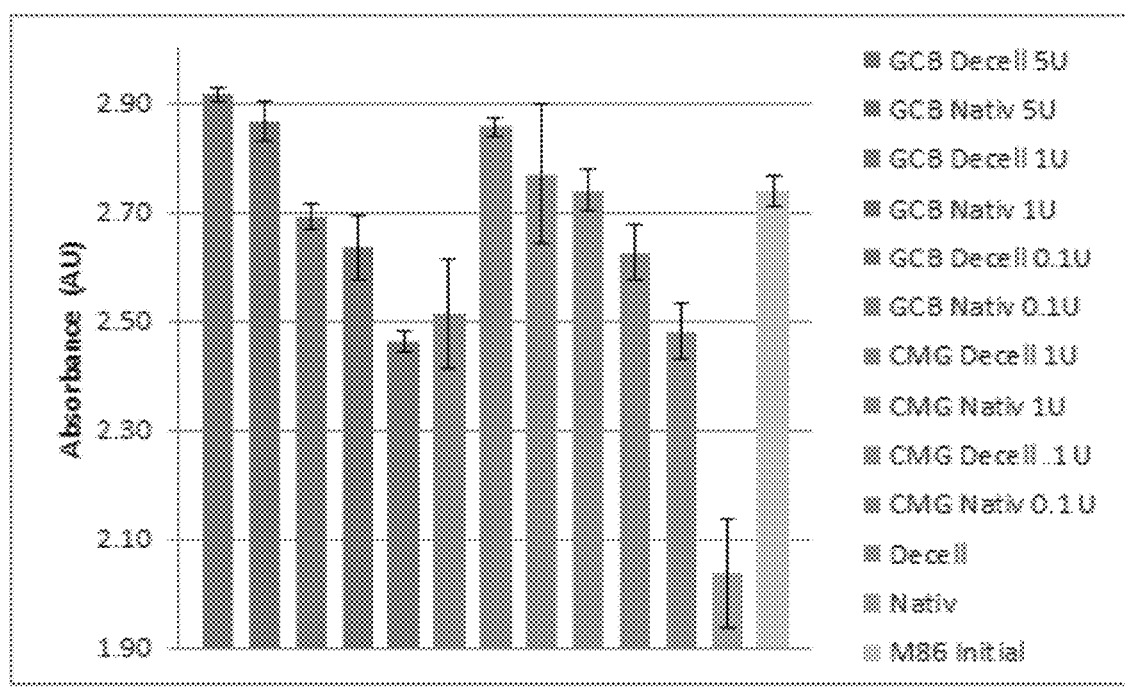
FIG. 4 is a graph depicting the absorption of M86 antibodies on native tissue with and without decellularization and treatment with α-galactosidase.

FIG. 4 shows the absorption of M86 antibodies on treated tissue. In the graph, two types of tissue are compared: native tissue, which has not been decellularized, and decellularized tissue. Comparison values are contained on the right-hand side of the graph: M86 initial, Nativ and Decell give the absorption values for tissue that has not been treated with α-galactosidase. Here, the native tissue demonstrates the highest value of α-gal epitopes. M86 initial specifies the absorption at which no absorption of the antibodies has taken place. This value constitutes the limit value for tissue on which α-gal epitopes are no longer present. From the comparison of M86 initial, Nativ and Decell, it can be seen that the decellularization already removes a significant quantity of α-gal epitopes (comparison of Decell and Nativ). However, it is also clear that a significant quantity of α-gal epitopes remain on the tissue (comparison of Decell and M86 initial).

The further absorption data shows the influence of the treatment with α-galactosidases on the concentration of α-gal epitopes on the surface of the tissue. The α-galactosidases of green coffee bean (GCB, Sigma Aldrich) at a concentration of 1 unit per ml could not remove all α-gal epitopes (comparison of M86 initial and GCB*5 U). However, due to the use of 1 U of the α-galactosidase of green coffee bean, the concentration of α-gal epitopes on the surface is considerably reduced (comparison of Decell/Nativ and GCB*1 U). If the high concentration of 5 Units per ml of the α-galactosidase of green coffee bean is used, practically all α-gal epitopes on the surface of the tissue can be removed (comparison of M86 initial and GCB*5 U). The extraordinary suitability of the α-galactosidase of *Cucumis melo* (CMG, *Cucumis melo* galactosidase) will be explained hereinafter on the basis of FIG. 4. If the comparatively low concentration of 1 unit per ml is used, all α-gal epitopes on the surface of the tissue can be removed (comparison of M86 initial with CMG*1 U). It has also been found that in the case of decellularized tissue just ¹/₁₀ of a unit is sufficient to remove practically all α-gal epitopes on the surface of the tissue (comparison of M86 initial with CMG Decell 0.1 U). In the case of native tissue approximately all α-gal epitopes on the surface of the tissue are removed at this extremely low concentration (comparison of M86 initial with CMG Native 0.1 U). It has thus been found that α-galactosidases of *Cucumis melo* can remove α-gal epitopes on the surface of the tissue in a highly efficient manner, and moreover much better than α-galactosidases of green coffee bean.

Figure 5:
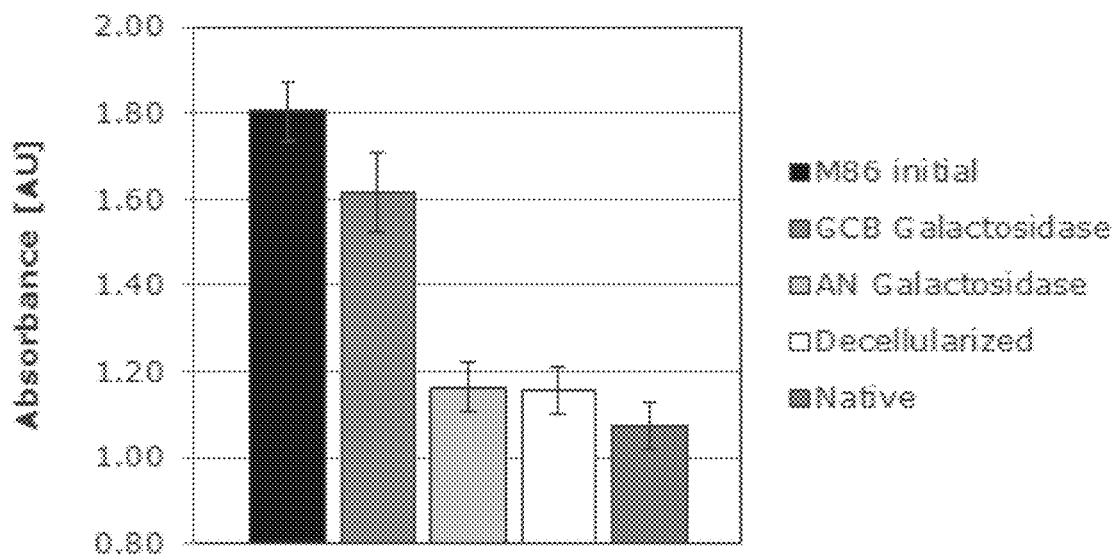
FIG. 5 is a graph depicting the absorption of M86 antibodies on native tissue with and without decellularization and treatment with an α-galactosidase of *Aspergillus niger*.

FIG. 5 shows, in addition to the above data in FIG. 4, the relative performance of an α-galactosidase of *Aspergillus niger*. Again, the comparison values of M86 initial, Native and Decellularized are shown, wherein M86 initial again describes the value at which it is assumed that α-gal epitopes are no longer present on the surface of the tissue, whereas Native and Decellularized specify the values of tissue that has not been treated with α-galactosidase. Native tissue at a concentration of 5 units/ml forms the basis. It can be seen, as already clear from FIG. 4, that the α-galactosidase of green coffee bean (GCB) is able to remove α-gal epitope on the surface of the tissue. By comparison, however, it can be seen that the acidic α-galactosidase of *Aspergillus niger* (AN) is hardly able at this concentration to remove α-gal epitopes on the surface of the tissue.

EXAMPLES

Hereinafter, an embodiment of an entire method for preparing biological tissue for implant applications according to the present proposal will be described in detail in 12 steps.

In step 1, a pericardium is removed from a pig in a slaughterhouse and is stored in a sterile isotonic sodium chloride solution (9 g/l; Fresenius-Kabi) at a temperature of 4° C. for 2 hours. The solution contains sodium chloride as well as penicillin and/or streptomycin to kill bacterial germs.

In step 2, the tissue is prepared, moist, in a sodium chloride solution (9 g/l; Fresenius-Kabi). That is, the layers of the pericardium are separated from one another, adhering fatty and connective tissue is carefully removed, and the tissue is cut to the size and shape for the desired application.

Figure 6:
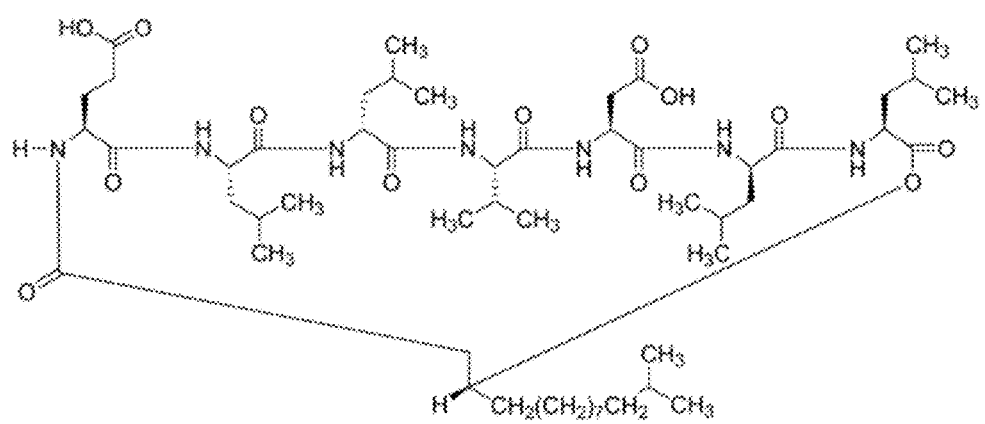
FIG. 6 is a drawing of the structural formula of surfactin.

After rinsing with a sodium chloride solution (9 g/l; Fresenius-Kabi) with slight movement of the tissue in step 3, the tissue is decellularized in step 4. The decellularization in step 4 takes place with a detergent comprising a buffer solution containing surfactin (the structure of surfactin is depicted in FIG. 6). In this exemplary embodiment of the invention, surfactin (Sigma-Aldrich, surfactin from *Bacillus subtilis*, Art. No. 53523) having a concentration of 600 mg/l is dissolved in a DPBS phosphate buffer solution (Lonza; DPBS w/o Ca++/Mg++; Art. No. 17-512). The tissue remains in this washing solution for 20 hours at 37° C. The tissue is then cleaned nearly entirely of cellular components located therein without substantially changing the structure of the collagen fibers.

In step 5 the tissue is rinsed in 100 ml sodium chloride solution (9 g/l; company Fresenius-Kabi) at room temperature with slight movement. Step 5 is repeated here in this exemplary embodiment of the invention 8 times for 10 minutes.

The tissue is then treated in step 6 with α-galactosidase of *Cucumis melo* with a concentration of 1 unit per ml (1 U/ml) in DPBS at room temperature and a pH of 7.4 for 24 hours and is then rinsed with 200 ml DPBS. The rinsing process is repeated here six times. The α-galactosidase of *Cucumis melo* was commercially obtained from Sigma Aldrich.

In step 7 the tissue is rinsed for 10 minutes at 37° C. with 100 ml of a 70% ethanol solution. In step 8 a further rinsing step in 100 ml sodium chloride solution (9 g/l; company Fresenius-Kabi) is performed with slight movement.

In step 9 the collagen fibers are cross-linked with a cross-linking agent. In this exemplary embodiment of the invention the tissue is placed for 48 hours at a temperature of 4° C. in a solution containing glutaraldehyde (company Sigma-Aldrich, product no. F5882) at pH 7.4. The glutaraldehyde-containing solution consists of glutaraldehyde with a concentration of 6 g/l in DPBS without calcium and magnesium (company Lonza; DPBS w/o Ca++/Mg++; product no. 17-512).

Step 10 repeats step 9 at room temperature. Step 10 is carried out for 14 days, wherein the solution is replaced every 48 hours.

In step 11 the tissue is rinsed in this exemplary embodiment of the invention 6 times for 20 minutes at room temperature with slight movement with 100 ml sodium chloride solution (9 g/l; company Fresenius-Kabi). After a rinsing process in step 11, the tissue can be stored in glutaraldehyde or processed further in step 12

The exemplary embodiment described here is intended to clarify the invention. The number and/or design of the rinsing steps (in particular the concentration and composition of the solution for rinsing, or of the buffer solution) can be varied by a person skilled in the art as he sees fit.

What is claimed is:

1. A method for preparing tissue for medical applications, comprising:
   decellularizing the tissue by means of a detergent, characterized in that the decellularizing detergent contains at least one amphiphilic lipopeptide;
   treating the decellularized tissue with an α-galactosidase; and
   cross-linking the collagen fibers of the treated tissue by means of a suitable cross-linking agent.

2. The method according to claim 1, characterized in that the decellularizing detergent contains a cyclic lipopeptide.

3. The method according to claim 2, characterized in that the cyclic lipopeptide is surfactin.

4. The method according to claim 1, characterized in that the lipopeptide is surfactin at a concentration in the detergent of 100 mg/L to 2000 mg/L.

5. The method according to claim 4, wherein the surfactin is at a concentration in the detergent of 500 mg/L to 700 mg/L.

6. The method according to claim 1, characterized in that the detergent contains daptomycin, caspofungin, arthrofactin, an echinocandin, an iturin, a syringomycin, a syringopeptide, and/or a polymyxin.

7. The method according to claim 1, characterized in that the detergent contains a buffer solution.

8. The method according to claim 1, characterized in that the α-galactosidase is an alkaline α-galactosidase.

9. The method according to claim 1, characterized in that the α-galactosidase is a GH-36 family α-galactosidase enzyme.

10. The method according to claim 1, characterized in that the α-galactosidase is a GH-36 family, sub-group II α-galactosidase enzyme.

11. The method according to claim 1, characterized in that the α-galactosidase is a *Cucumis melo* enzyme.

12. The method according to claim 1, characterized in that the cross-linking agent contains glutaraldehyde, a carbodiimide, formaldehyde, a glutaraldehyde acetal, an acyl azide, a cyanimide, genipin, a tannin, pentagalloyl glucose, a phytate, a proanthocyanidin, reuterin and/or an epoxide compound.

13. The method according to claim 1, characterized in that the tissue is rinsed before and/or after decellularization at least once with a suitable solvent.

14. The method according to claim 1, wherein the tissue is for an artificial heart valve.

* * * * *